(12) United States Patent
Jerri et al.

(10) Patent No.: US 9,968,096 B2
(45) Date of Patent: May 15, 2018

(54) PROCESS FOR PREPARING ANTIMICROBIAL MICROCAPSULES

(71) Applicant: Firmenich SA, Geneva (CH)

(72) Inventors: Huda Jerri, Plainsboro, NJ (US); Marlène Jacquemond, Geneva (CH); Brian MacDougall, Plainsboro, NJ (US)

(73) Assignee: Firmenich SA, Geneva (CH)

( * ) Notice: Subject to any disclaimer, the term of this patent is extended or adjusted under 35 U.S.C. 154(b) by 0 days. days.

(21) Appl. No.: 15/322,040

(22) PCT Filed: Jun. 25, 2015

(86) PCT No.: PCT/EP2015/064341
§ 371 (c)(1),
(2) Date: Dec. 23, 2016

(87) PCT Pub. No.: WO2015/197745
PCT Pub. Date: Dec. 30, 2015

(65) Prior Publication Data
US 2017/0142974 A1 May 25, 2017

(30) Foreign Application Priority Data

Jun. 27, 2014 (EP) ..................................... 14174840

(51) Int. Cl.
*A01N 59/16* (2006.01)
*B01J 13/16* (2006.01)
*C11B 9/00* (2006.01)

(52) U.S. Cl.
CPC .............. *A01N 59/16* (2013.01); *B01J 13/16* (2013.01); *C11B 9/0015* (2013.01)

(58) Field of Classification Search
None
See application file for complete search history.

(56) References Cited

U.S. PATENT DOCUMENTS

| 4,880,721 | A | * | 11/1989 | Ishikawa | ............... G03F 7/002 428/402.2 |
| 2004/0247690 | A1 | * | 12/2004 | Yang | .................... B01J 13/02 424/490 |
| 2007/0202063 | A1 | | 8/2007 | Dihora et al. | |

FOREIGN PATENT DOCUMENTS

| CN | 1966848 A | 5/2007 |
|---|---|---|
| CN | 1966848 A | 5/2007 |
| CN | 1966849 A | 5/2007 |
| EP | 1741775 B1 | 4/2009 |
| GB | 2 432 852 A | 6/2007 |
| GB | 2432850 A | 6/2007 |
| GB | 2432851 A | 6/2007 |
| GB | 2432852 A | 6/2007 |
| GB | 62432843 A | 6/2007 |
| WO | WO2003048090 A1 | 6/2003 |
| WO | WO2003055588 A1 | 7/2003 |
| WO | WO2005054422 A1 | 6/2005 |
| WO | WO2007062733 A1 | 6/2007 |
| WO | WO2007062833 A1 | 6/2007 |
| WO | WO2007096592 A1 | 8/2007 |
| WO | WO2008018684 A1 | 2/2008 |
| WO | WO2010146556 A2 | 12/2010 |
| WO | WO2013000587 A1 | 1/2013 |

OTHER PUBLICATIONS

International Search Report and Written Opinion, application PCT/EP2015/064341, dated Jul. 6, 2016.
Kvitek et al., Journal of Physics: Conference Series 304 (2011) 012029.
Panacezk et al., J. Phys. Chem. B, 2006, 110(33), p. 16248.
Radziuk et al., Langmuir, 2007, vol. 23, p. 4612-4617.
Qingwen et al., Polymer, Vol. 48, 2007, p. 3317-3323.

* cited by examiner

*Primary Examiner* — Aradhana Sasan
(74) *Attorney, Agent, or Firm* — Winston & Strawn LLP

(57) ABSTRACT

More particularly, the present invention relates to a process for producing antimicrobial core-shell microcapsules with immobilized silver particles into and onto the shell. The latter can be used in home or personal care products for delivering a perfuming and malodor-countering effect. The microcapsules obtainable by such a process and the consumer products comprising these microcapsules are also objects of the invention.

20 Claims, No Drawings

PROCESS FOR PREPARING ANTIMICROBIAL MICROCAPSULES

This application is a 371 filing of International Patent Application PCT/EP2015/064341 filed 25 Jun. 2015, which claims the benefit of European patent application n° 14174840.0 filed 27 Jun. 2014

TECHNICAL FIELD

The present invention relates to the field of delivery systems. More particularly, the present invention relates to a process for producing core-shell microcapsules with immobilized silver particles into and onto the shell which provide an antimicrobial activity to the capsules. The latter can be used in home or personal care products for delivering a perfuming effect together with an antimicrobial effect. The microcapsules obtainable by such a process and the consumer products comprising these microcapsules are also objects of the invention.

PRIOR ART

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner. Polyurea capsules, formed by interfacial polymerisation between a polyisocyanate and a polyamine, are well known capsules that are used in a large variety of technical fields, including perfumery.

Polyurea-based microcapsules are often incorporated into personal and household care products wherein, in addition to delivering a perfume to impart a hedonic effect, an antimicrobial activity would be needed in order to slow down or prevent malodor formation. Combination of antimicrobial properties and perfume long-lasting and therefore a dual release delivery system would thus be desirable.

Addition of antimicrobial agents or of malodor counteracting compositions formed of mixtures of perfumery materials have been described e.g in WO2010146556 as possibly incorporate directly to personal and household care products. However this solution does not provide a long-lasting effect of the antimicrobial activity.

Multifunctional capsules with an inner oil core and presenting an antimicrobial activity have also been disclosed in WO03055588. In this publication, long-lasting antimicrobial effects in conjunction with the controlled release of functional substance from the core phase are obtained by adhering silver nanoparticles to the outer shell of the microcapsules containing functional substances such as a perfume composition in the inner core of the capsules. The method of preparing these silver nanoparticle-containing functional microcapsules includes treating the microcapsules with a pre-made silver nanoparticle solution dispersed in a water-soluble styrene maleic anhydride solution before hardening of the outer shell. However, said process presents the drawback of the presence of free silver nanoparticles in the microcapsule slurry and it further requires several process steps. Moreover, the loading of silver nanoparticles into the microcapsules and the control of the size of the silver nanoparticles used is not optimized.

The present invention advantageously provides a solution to the above mentioned problems through a process that allows the in-situ nucleation and growth of silver particles during an interfacial polymerization conducted in a presence of an anionic emulsifier.

SUMMARY OF THE INVENTION

The invention relates to a novel process to prepare microcapsules, which avoids the problems from the prior art. Unexpectedly the formation of silver particles during the interfacial polymerization conducted in the presence of an anionic emulsifier leads to microcapsules able to deliver active ingredients, such as perfumes together with antimicrobial agents while reducing the amount of free particles in solution.

A first object of the present invention is therefore a process for the preparation of antimicrobial polyurea-based core-shell microcapsules comprising, a) dissolving at least one polyisocyanate in an active ingredient, preferably a perfume to form an oil phase;

b) dispersing the oil phase into an aqueous solution comprising an anionic emulsifier to form an oil-in-water emulsion;

c) adding to the oil-in-water emulsion a polyamine, a silver salt and a reducing agent provided that the reducing agent is added after the silver salt;

to form microcapsules with polyurea-based walls comprising silver particles in or on the walls.

A second object of the present invention consists of antimicrobial polyurea-based microcapsules obtainable by the process described in the first object, comprising a perfume-based core and silver particles in or on the shell.

A third object of the present invention is a perfuming composition comprising a) as perfuming ingredient, antimicrobial polyurea-based microcapsules as defined above;

b) at least one ingredient selected from the group consisting of a perfumery carrier and a perfumery co-ingredient.

Another object of the present invention is a perfuming consumer product comprising the antimicrobial polyurea-based microcapsules.

A last object of the present invention is the use of the antimicrobial polyurea-based microcapsules as defined above, containing perfume to provide a combined long-lasting antimicrobial effect and fragrance release.

DETAILED DESCRIPTION OF THE INVENTION

The process of this invention advantageously allows obtaining polyurea-based microcapsules which release antimicrobial agents and perfumes, by combining an interfacial polymerization process together with silver nanoparticles formation. This novel process leads to the formation of core-shell microcapsules comprising silver nanoparticles on or in the shells of the microcapsules.

More particularly, the present invention advantageously solves the above-mentioned problems by adding a silver salt and then a reducing agent during the process of the preparation of the polyurea-based microcapsules, and more specifically after the formation of the oil in water emulsion.

Therefore, a first object of the present invention is a process for the preparation of antimicrobial polyurea core shell microcapsules comprising the following steps:

a) dissolving at least one polyisocyanate in an active ingredient, preferably a perfume to form an oil phase;

b) dispersing the oil phase into an aqueous solution comprising an anionic emulsifier to form an oil-in-water emulsion;

c) adding to the oil-in-water emulsion a polyamine, a silver salt and a reducing agent provided that the reducing agent is added after the silver salt;

to form microcapsules with polyurea-based walls comprising silver particles in or on the walls.

By "polyurea-based" wall or shell or microcapsules, it is meant that the polymer comprises urea linkages produced by either an amino-functional crosslinker or hydrolysis of isocyanate groups to produce amino groups capable of further reacting with isocyanate groups during interfacial polymerization.

In the process of the invention, silver particles are advantageously formed in situ during the interfacial polymerization by the reduction of silver salts with a reducing agent. The silver salts interact with the anionic emulsifier at the oil/water interface leading to silver particles formation on or in the microcapsule shells after the reduction of to the silver salt. The process provides an antimicrobial activity together with long lasting of e.g. a fragrance while limiting/avoiding the presence of free silver particles which was one of the problems from solutions known heretofore.

The antimicrobial property of silver particles which is well established in literature with a broad spectrum of action against bacteria (see for example *Nanosafe*2010: *International Conference on Safe Production and Use of Nanomaterials* and *Journal of Physics: Conference Series* 304 2011 012029), is attributed to the release of silver cations triggered by moisture.

According to the present invention, the in situ formation of silver nanoparticles also unexpectedly enables higher loading of the silver nanoparticles in or on the wall of the capsules compared to the prior art wherein electrostatic interactions between premade particles was leading to a lower loading.

The formation of silver particles by the reduction of silver salts with a reducing agent is well documented in the literature (*J. Phys. Chem. B* 2006, 110 (33), 16248, *Langmuir* 2007, 23 (8), 4612 and references wherein). But the use of this type of reaction in situ, during the polyurea-based microcapsule formation is novel and presents several unexpected advantages as mentioned above.

The silver salts and the reducing agents used in the process of the invention are selected amongst those described in the literature. Non-limiting examples of appropriate silver salts are selected from the group consisting of silver nitrate, silver citrate, silver chloride, silver iodide, silver sulphate and silver bromide. More preferably, the silver nitrate is used in the process of the invention.

The silver salt is used in an amount of between 0.01 and 10% and more preferably between 0.1 and 1.0% by weight, relative to the total weight of the obtained microcapsules slurry.

Non-limiting examples of appropriate reducing agents are selected from the group consisting of sodium borohydride, mono and disaccharides (e.g. glucose or maltose), sodium citrate, ascorbic acid, ascorbate, formic acid, formites, earth metals, oxalic acid, hydrazine, lithium aluminum hydride, and other synthetic or naturally-derived reducing agents which oxidize during a chemical reaction. More preferably, the sodium borohydride is used in the process of the invention.

The silver salt and the reducing agent are mainly used in a weight ratio comprised between 1:1 and 5:1. The weight and volume ratios of the silver salt and reducing agent solutions is a function of the nature of the silver salt and reducing agent and the person skill in the art is well able to select the most convenient ratios in each case to optimize the reaction. The amount of both compounds allows controlling the size and the loading of the silver nanoparticles on or in the shell of the microcapsules. Preferably, an aqueous solution of silver salt and an aqueous solution of reducing agent are used.

The microcapsules obtained preferably comprise between 100 and 10000 ppm of silver particles, more preferably between 350 and 5000 ppm of silver particles.

In the first step of the process according to the invention, at least one polyisocyanate is dissolved in an active ingredient, preferably a perfume to form an oil phase.

By "perfume" (or also "perfume oil") it is meant here a perfume that is liquid at about 20° C. According to any one of the above invention embodiments said perfume oil in which the polyisocyanate is dissolved in step a) can be a perfuming ingredient alone or a mixture of ingredients. By "perfuming ingredient" it is meant here a compound, which is used in a perfuming preparation or a composition to impart a hedonic effect. In other words such an ingredient, to be considered as being a perfuming one, must be recognized by a person skilled in the art as being able to impart, modify or modulate in a positive or pleasant way the odor of a composition, and not just as having an odor. The perfuming ingredient may also impart a pleasant odor by masking or neutralizing unpleasant odors.

The nature and type of the perfuming ingredients do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

The perfuming ingredient(s) to be encapsulated may be dissolved in a solvent of current use in the perfume industry thus the core of the capsule might be pure perfuming ingredients or a mixture of perfuming ingredients in an adequate hydrophobic solvent. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn®. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

The invention can also be performed with another active ingredient than a perfume, that would benefit from an encapsulation, for instance a dye, dye precursor, catalyst from chemical reactions, adhesive, reactive substance for adhesive applications, pharmaceutical active substance, cosmetic active substance, plant protection active substance (for example insecticide, fungicide, herbicide), water repellent, flame retardant, sunscreen agent or solvent.

According to preferred embodiments of the invention, there is used an amount of between 10 and 60%, more preferably between 20 and 50% of active ingredient in the process of the invention, these percentages being defined by weight relative to the total weight of the obtained microcapsules.

Preferably, the perfume used in the process of the invention contains less than 10% of its own weight of primary alcohols, less than 15% of its own weight of secondary alcohols and less than 20% of its own weight of tertiary alcohols. Advantageously, the perfume used in the process of the invention does not contain any primary alcohols and contains less than 15% of secondary and tertiary alcohols. Such limited amounts of alcohols have the advantage of reducing the amount of isocyanate functional groups reacting with the perfume.

The at least one polyisocyanate used in the process of the invention comprises at least two isocyanate groups. Preferably it contains at least three isocyanate groups. The polyamine added in step c) of the process will react with those functional groups by interfacial polymerization to form the core-shell structure of the capsules. Following these numbers of functional groups, an optimal reticulation or network of the capsules wall will be achieved, providing thus microcapsules exhibiting a prolonged slow release of fragrances, as well as an improved stability in the consumer product. Low volatility polyisocyanate molecules are preferred.

The polyisocyanate may be aliphatic, aromatic or a mixture of both aromatic and aliphatic ones. In the case of mixtures of polyisocyanates, each member of the mixture has at least two isocyanate functional groups. Preferably, the at least one polyisocyanate is in the form of a mixture of at least one aliphatic polyisocyanate and of at least one aromatic polyisocyanate, both comprising at least two isocyanate functional groups.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-11ON). In a most preferred embodiment, the aromatic polyisocyanate is a trimethylol propane-adduct of xylylene diisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

Examples of preferred specific mixtures of at least one aliphatic polyisocyanate and of at least one aromatic polyisocyanate are a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

In a preferred embodiment, the at least one aliphatic polyisocyanate and the at least one aromatic polyisocyanate are used in a respective molar ratio comprised between 80:20 and 10:90, preferably between 75:25 and 20:80, more preferably between 60:40 and 20:80, even more preferably between 60:40 and 30:70, most preferably between 45:55 and 30:70.

Preferably the polyisocyanate mixture is added in an amount comprised between 2 and 30% by weight, relative to the total weight of the solution obtained in step a).

According to another preferred embodiment, the polyisocyanate is an aromatic (poly)isocyante and is added in an amount comprised between 2 and 20% by weight, relative to the total weight of the solution obtained in step a).

In step b) of the process of the present invention, the oil phase is dispersed into an aqueous solution comprising an anionic emulsifier to form a water-in-oil emulsion. An anionic emulsifier is used in order to absorb the cationic silver salt onto the droplet surface before adding the reducing agent.

The term "emulsion" is meant to designate here the fact that the oil phase obtained in step a) is dispersed in an aqueous solution. The term "emulsion" is therefore understood as emulsion or dispersion. The presence of an emulsifier in the aqueous solution allows the stabilization of the oil droplets therein. In the present invention a colloidal stabilizer could be used as emulsifier. The emulsion may be prepared by high shear mixing and adjusted to the desired droplet size. The droplet size can be checked with light scattering measurements or microscopy. This procedure does not require a more detailed description here as it is well known to a skilled person in the art.

Non limiting examples of anionic emulsifier include acylglycinate salts (such as that sold by Ajinomoto under the trade name Amilite®), polyvinyl alcohol (such as that sold by Kuraray under the trade name Mowiol® KL-506 18-88), cellulose polymers for example sodium carboxymethylcellulose polymers, such as those sold by Hercules under the trade name Ambergum®, sodium dodecyl sulfate, Stepantex® (commercially available from Stepan), polyvinyl pirrolidone, anionic polyelectrolytes, bovine serum albumin and gum arabic. Preferably, the anionic emulsifier used in the process of the invention is polyvinyl alcohol.

Preferably the anionic emulsifier is added in an amount comprised between 0.1 and 10% by weight, relative to the total weight of the of the obtained microcapsules slurry and more preferably between 0.3 and 1% by weight, relative to the total weight of the obtained microcapsules slurry.

In step c) of the process of the invention, a polyamine, an aqueous solution of silver salt and an aqueous solution of reducing agent are added in any order to the emulsion provided that the reducing agent is added after the silver salt.

The polyurea-based wall of the microcapsules is the result of the interfacial polymerisation between the polyisocyanate dissolved in step a) and the polyamine added in step c). The silver salts added at this step interact with the anionic emulsifier which is around the perfume oil droplets. The silver cations are electrostatically adsorbed on the surface of the oil droplets and are then reduced by the reducing agent, providing formation of silver nanoparticles immobilized on or in the shell of the microcapsules.

For the purpose of the present invention, the polyamine may be used alone or be admixed with glycerin.

Preferably said polyamine is selected from the group consisting of 1,2diaminopropane, 1,2-diaminoethane, diethylenetriamine, water soluble guanidine salts, guanidine, tris-(2-aminoethyl)amine, N,N'-bis(3-aminopropyl)-ethylenediamine, N,N,N',N'-tetrakis(3-aminopropyl)-1,4-butanediamine and 3,5-diamino-1,2,4-triazole.

More preferably, the polyamine is selected from the group consisting of 3,5-diamino-1,2,4-triazole, water soluble guanidine salts, guanidine, tris-(2-aminoethyl)amine, N,N'-bis(3-aminopropyl)ethylenediamine and N,N,N',N'-tetrakis (3-aminopropyl)-1,4-butanediamine Most preferably it is selected from 3,5-diamino-1,2,4-triazole, guanidine, water-soluble guanidine salts and N,N'-bis(3-aminopropyl)-ethylenediamine. By "water soluble guanidine salt" it is meant a salt soluble in water and resulting from the reaction of guanidine with an acid. One example of such salts is guanidine carbonate.

The amount of polyamine used is typically adjusted so that, for each mole of isocyanate group dissolved in the perfume of step a), there is added from 0.5 to 3 moles of amine groups in step c). Preferably, for each mole of isocyanate group dissolved in the perfume in step a), 1 to 3, more preferably 1 to 2 moles of amine groups are added in step c).

No specific action is required to induce the polymerisation between the polyisocyanates and the polyamine. The reaction starts immediately after adding the polyamine. Preferably the reaction is maintained for 2 to 15 hours, more preferably for 2 to 10 hours.

The silver salt and the polyamine can be added at any time after the oil in water emulsion of step b) is formed. The reducing agent must be added after addition of the silver salts in order to minimize the amount of free silver nanoparticles in solution.

More preferably, the silver salt is added after the formation of the oil in water emulsion following by the reducing agent and the polyamine is added at the last stage.

The specific composition of the wall of the capsule is key in obtaining antimicrobial microcapsules that are at the fine balance between release and retention so as to achieve satisfactory release of active ingredients, such as a fragrance and silver cations, once the capsules are placed on textiles or other substrates, while showing the desired stability in the end product base (e.g. counteracts efficiently the extraction of the perfume by the surfactants of the consumer product). Therefore careful selection of the polyamine and of the polyisocyanate, among the ones mentioned above, enables the fine tuning of the properties and stability of the capsules.

In an optional step of the process of the invention, the microcapsules are washed via centrifugation and re-suspension several times. In another optional step, the microcapsules can be isolated from the slurry that is obtained from the process described. In another optional step, the microcapsules slurry can be dried in a generally known manner to form a powder of functionalized polyurea-based microcapsules. Any drying method known to a person skilled in the art can be used and in particular the slurry may be spray dried to provide a microcapsule powder.

Antimicrobial core-shell polyurea-based microcapsules obtainable by the process of any of the above-described embodiments comprising a perfume-based core and silver particles in or on the shell are also an object of the present invention. Therefore the present invention also provides microcapsules comprising
 a polyurea-based wall, which comprises the reaction product of the polymerization between at least one polyisocyanate and at least one polyamine;
 a silver particle on or in the polyurea-based wall
 an anionic emulsifier; and
 an encapsulated perfume;
 characterized in that the silver particles are generated during the interfacial polymerisation.

The incorporation of the silver particles in or on the wall of the microcapsules results in long-lasting antimicrobial effects in conjunction with the release of fragrance.

The microcapsules obtained have an average diameter (d(v, 0.5)) comprised between 1 and 50 μm and preferably comprised between 5 and 35 μm, more preferably between 5 and 25 μm. In the present context, "average diameter" refers to the arithmetic mean.

Silver particles made following the process of the invention have a roughly spherical shape or a prism triangular shape and with a size comprised between 5 and 500 nm and more preferably between 50 and 300 nm. The silver nanoparticles are highly localized on the capsule shell but are also embedded into the surface.

The polyisocyanate, the perfume, the emulsifier, the polyamine, the silver salt and the reducing agent, as well as their respective amounts in the capsules, are as defined above in any embodiment related to the process of the invention for the preparation of the microcapsules.

The microcapsules of the present invention can comprise other optional ingredients such as antioxidants, deposition aids, antimicrobial agents or antifoaming agents.

As shown in the examples below, the antimicrobial polyurea microcapsules obtained by the process of the invention provide particularly good antimicrobial activity.

The microcapsules of the invention can be advantageously used for the controlled release of the encapsulated perfume and of the antimicrobial ions. It is therefore particularly appreciated to include these microcapsules as perfuming and antimicrobial ingredients in a perfuming composition or in a perfumed consumer product. The invention also relates to methods of perfuming and malodor countering via the use of the microcapsules of the invention.

Therefore, another object of the present invention is a perfuming composition comprising:
 i) as perfuming ingredient, microcapsules as defined above;
 ii) at least one ingredient selected from the group consisting of a perfumery carrier and a perfumery co-ingredient; and
 iii) optionally at least one perfumery adjuvant.

By "perfumery carrier" we mean here a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

"Perfuming co-ingredient" designates and ingredient, the nature of which is equivalent to perfume ingredient defined above.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of the invention's antimicrobial microcapsules as defined above and at least one perfumery carrier represents a particular embodiment of the invention.

According to a particular embodiment of the invention, the perfuming composition is devoid of free silver particles.

Furthermore, antimicrobial microcapsules as defined above or a perfuming composition comprising such microcapsules can also be advantageously used in all the fields of modern perfumery, i.e. fine or functional perfumery, to prevent the malodor formation related to microbial activity and to positively impart or modify the odor of a consumer product and into which said microcapsules as defined above are added.

As shown in the examples below, the antimicrobial polyurea-based microcapsules obtained by the process of the invention provide, in addition to particularly good olfactive performance, a good antimicrobial activity. They provide a controlled or triggered release of the encapsulated perfume and of the silver cations responsible for the antimicrobial activity, said perfume and silver cations being slowly released from the microcapsules, thus considerably improving the antimicrobial and perfume long-lastingness and intensity.

Consequently, another object of the present invention is represented by a perfuming consumer product comprising, as perfuming ingredient, microcapsules as defined above.

The invention's microcapsules can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's microcapsules. For the sake of clarity, said perfuming consumer product is a non-edible product.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent or refresher; or a malodor neutralizing sanitary product; or a pet product in the form of absorbent pads, litters, cleansers and refreshing and perfuming sprays and products.

The capsules slurry obtained in the process of the invention may be used as such to perfume the consumer products, in which case the reaction mixture is directly added to a consumer product as defined in any of the above embodiments. Alternatively, the microcapsules obtained in the process of the invention may be isolated from the reaction mixture before being incorporated into the consumer product. Similarly, the reaction mixture comprising the microcapsules of the invention may be mixed with or sprayed onto a dry, powdered product, such as a washing powder or powdered detergent or the microcapsules may be dried and added to these products in solid form. The microcapsules may for example be spray-dried.

The proportions in which the microcapsules according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.01% to 1% by weight, can be used when these compounds are incorporated into perfumed articles, percentage being relative to the weight of the article.

Formulations of consumer product bases in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

The last object of the present invention is the use of the antimicrobial polyurea-based microcapsules, containing perfume to provide antimicrobial effects and fragrance release.

EXAMPLES

The following non limiting examples are further illustrative of the present invention embodiments, and further demonstrate the advantages of the invention devices relative to prior art teachings.

Abbreviations have the usual meaning in the art and the temperatures are indicated in degrees centigrade (° C.).

Example 1

Preparation of Antimicrobial Polyurea-Based Microcapsules According to the Invention General Procedure:

At least one polyisocyanate (Takenate® D-110N, trademark from Mitsui Chemicals and/or Desmodur® N100, trademark from Bayer) was dissolved in a perfume. The solution was poured into a PVOH aqueous solution and emulsified for 4 min using an Ultra-Turrax T25 disperser at 2400 rpm to form an Oil-in-Water (O/W) emulsion. This emulsion was stirred at 400 rpm using a mechanical overhead stirrer and, a silver salt aqueous solution was added. The emulsion was stirred 15 min and then a reducing agent was added. The emulsion was stirred 15 min and the pH was adjusted to 10.5-11 by adding a NaOH aqueous solution (50 weight % in water). Then, a polyamine e.g. guanidine carbonate was slowly added during 1 h. Once the addition of the polyamine was finished, the reaction temperature was gradually elevated to between 50 and 75° C. during 1 h and was kept at 70° C. for 2 h. Finally, the formed capsule slurry was cooled down to room temperature.

Polyurea-based microcapsules according to the invention (Capsules A) were prepared according to this general procedure, with the following ingredients.

TABLE 1

Composition of Capsules A

| Ingredient | Amount (g) |
| --- | --- |
| Delta Damascone[1] | 30.00 |
| Takenate ® D 110N[2] | 4.38 |
| 1% PVOH Solution[3] | 45.00 |
| Silver Nitrate | 0.054 |
| Water for AgNO$_3$ Solution | 1.00 |
| Sodium Borohydride | 0.06 |
| Water for NaBH$_4$ Reducing Agent Solution | 3.5 |
| Guanidine Carbonate[4] | 0.9 |
| Water for Guanidine Carbonate | 5.00 |

TABLE 1-continued

Composition of Capsules A

| Ingredient | Amount (g) |
| --- | --- |
| Top-Off Water | 10.00 |
| pH Adjust with 50% NaOH | 0.10 |

[1](E)-1-(2,6,6-trimethylcyclohex-3-en-1-yl)but-2-en-1-one, origin: Firmenich SA, Switzerland
[2]Trimethylol propane-adduct of xylylene diisocyanate, origin: Mitsui Chemicals, Inc., Japan
[3]KL506, origin: Kuraray Specialities Europe GmbH, Germany
[4]Origin: Alfa Aesar, USA

Example 2

Antimicrobial Activity of Capsules According to the Invention

The in vitro activity of capsules according to Example 1 against bacteria considered largely susceptible to currently utilized antimicrobials (American Type Culture Collection quality control organisms) as well as bacterial species associated with body odor was evaluated by determining the minimum inhibitory concentration (MIC) and minimum bactericidal concentration (MBC). Similarly-made control microcapsules without silver salt or reducing agent (negative control) were also evaluated. The composition of the control is similar to that of capsules A, except that reducing agent and silver salt have been substituted by top-off water. The isolates obtained from the American Type Culture Collection (ATCC) or from clinical laboratories were sub-cultured on the appropriate agar medium and incubated overnight at the appropriate conditions. The test organisms used in this study are listed in Table 2 below. Appropriate media were selected and employed to test aerobic and anaerobic isolates by broth macrodilution MIC assay in suitable chambers. Media were prepared according to the Clinical and Laboratory Standards Institute (CLSI) methods and were utilized at a 10× concentration to minimize the dilution of the test compounds in the assay. MIC values were determined using a broth macrodilution method as recommended by CLSI. All test agents were serial-diluted with a total of 11 two-fold dilutions and one growth control tube per test organism. The MIC was read and recorded as the lowest concentration of sample that inhibited significant visible growth of the organism relative to the solubility control and the growth control.

The MBC was determined essentially as described by CLSI (CLSI. *Methods for Determining Bactericidal Activity of Antimicrobial Agents; Approved Guideline*. CLSI document M26-A [ISBN 1-56238-384-1]. CLSI, 950 West Valley Road, Suite 2500, Wayne, Pa. 19087 USA, 1999). The viable count of each inoculum was determined prior to the inoculation of the MIC macrodilution tubes. From the standardized inoculum tube, serial 10-fold dilutions were made. Aliquots of 10-5 and 10-6 dilutions were spread on appropriate, duplicate plates and incubated at the appropriate conditions and counted manually. The average count of both dilution plates were used to calculate the viable inoculum count of the standardized tube. Following incubation of the macrodilution tubes and determination of MIC results, each MIC sample tube was vortexed and allowed to settle. Duplicate aliquots were removed from each negative growth well and were spotted onto agar plates appropriate for the test organisms. In the event that visible growth was difficult to read due to turbidity of the test formulations, all macrodilution tubes were sampled, prepared, and the numbers of colonies were counted manually. The sums of the counts for the two plates were compared to the values in the appropriate table of rejection values (CLSI. *Methods for Determining Bactericidal Activity of Antimicrobial Agents; Approved Guideline*. CLSI document M26-A [ISBN 1-56238-384-1]. CLSI, 950 West Valley Road, Suite 2500, Wayne, Pa. 19087 USA, 1999). These values are based upon the cell density of the inoculum and the target viable count reduction of 99.9%; if the sum of the colonies on duplicate plates was less than or equal to the value in the table, the concentration of drug in the sampled well is considered to be bactericidal. The MBC was then defined as the lowest concentration of agent to demonstrate a bactericidal effect. The observed MICs and MBCs of the evaluated agents are summarized in Table 2.

observed to occur below concentrations of 22% and as low as 2.8% which is impressive given the low silver content of the microcapsule prototype tested. Capsules of the invention were active against species of bacteria associated with malodor that were evaluated in this study (*S. epidermidis, S. hominis, Corynebacterium* spp., *P. acnes, M. luteus*, and *D. hominis*). These results indicate that the capsules of the invention are bactericidal against the majority of strains evaluated in the study, indicating that there is some antibacterial activity associated with these formulations above a certain threshold concentration. Higher silver content will likely provide greater antimicrobial activity.

TABLE 2

MIC and MBC results for capsules of Example 1 compared to microcapsules without silver (negative control). Results are given for % slurry or equivalent PPM for the capsules of Example 1.

| Organism | ATCC No. | Capsule of Example 1 (% Slurry) | | Capsule of Example 1 (PPM SILVER) | | Negative Capsule Control | |
|---|---|---|---|---|---|---|---|
| | | MIC (%) | MBC (%) | MIC (PPM) | MBC (PPM) | MIC (%) | MBC (%) |
| *Micrococcus luteus* | — | 0.18 | 5.6 | 0.6 | 19.5 | >90 | >90 |
| *Micrococcus luteus* | — | 1.4 | 2.8 | 4.9 | 9.7 | >90 | >90 |
| *Dermabacter hominis* | 51458 | 0.36 | 2.8 | 1.3 | 9.7 | >90 | >90 |
| *Staphylococcus hominis* | 27844 | <0.09 | 11 | 0.3 | 38.2 | >90 | >90 |
| *Staphylococcus hominis* | — | 0.18 | 22 | 0.6 | 76.5 | >90 | >90 |
| *Corynebacterium jeikeium* | 43734 | >90 | 22 | | 76.5 | >90 | >90 |
| *Corynebacterium striatum* | 6940 | >90 | 11 | | 38.2 | >90 | >90 |
| *Corynebacterium* spp. | — | >90 | 22 | | 76.5 | >90 | >90 |
| *Arcanobacterium haemolyticus* | 9345 | >90 | 11 | | 38.2 | >90 | >90 |
| *Propionibacterium acnes* | 6415 | <0.09 | 5.6 | 0.3 | 19.5 | >90 | >90 |
| *Propionibacterium acnes* | 11828 | 1.4 | 5.6 | 4.9 | 19.5 | >90 | >90 |
| *Propionibacterium acnes* | — | 2.8 | 11.25 | 9.7 | 39.1 | >90 | >90 |
| *Escherichia coli* | 25922 | >90 | 11 | | 38.2 | >90 | >90 |
| *Pseudomonas aeruginosa* | 27853 | 90 | 11 | 312.8 | 38.2 | >90 | >90 |
| *Haemophilus influenzae* | 49247 | >90 | 11 | | 38.2 | >90 | >90 |
| *Streptococcus pyogenes* | 49399 | 90 | 11 | 312.8 | 38.2 | >90 | >90 |
| *Enterococcus faecalis* | 29212 | 11.25 | 11.25 | 39.1 | 39.1 | >90 | >90 |
| *Staphylococcus aureus* | 29213 | >90 | 90 | | 312.8 | >90 | >90 |

The ability to distinguish an MIC at high concentrations for either Capsules of the invention or the Negative Control was hindered by the turbidity and insolubility of the formulations when tested at high concentrations. As expected, no activity (MIC or MBC) was observed with the negative control formulation against the evaluated isolates.

Observed MICs for the test formulations varied, and in several instances MBCs were observed where MICs were not apparent due to the insoluble nature of the test material and the associated turbidity in the absence of bacteria. The capsules according to the invention displayed activity against the majority of isolates evaluated by MBC, excluding *S. aureus* and *S. epidermidis*, and this activity was

What is claimed is:

1. A process for the preparation of antimicrobial polyurea-based core-shell microcapsules comprising the following steps:
   a) dissolving at least one polyisocyanate in an active ingredient to form an oil phase;
   b) dispersing the oil phase into an aqueous solution comprising an anionic emulsifier to form an oil-in-water emulsion;
   c) adding to the oil-in-water emulsion a polyamine, a silver salt and a reducing agent provided that the reducing agent is added after the silver salt; to form a slurry of microcapsules having polyurea-based walls comprising silver particles in or on the walls; and
   d) obtaining the microcapsules from the slurry.

2. The process according to claim 1, wherein the silver salt is selected from the group consisting of silver nitrate, silver citrate, silver chloride, silver iodide, silver sulphate and silver bromide.

3. The process according to claim 1 wherein the reducing agent is selected from the group consisting of sodium borohydride, mono and disaccharide, sodium citrate, ascorbic acid, formic acid, oxalic acid, hydrazine, lithium aluminium hydride, and ascorbate.

4. The process according to claim 1 wherein the silver salt is used in an amount comprised between 0.01 and 10% by weight, relative to the total weight of the microcapsules slurry.

5. The process according to claim 1 wherein the silver salt and the reducing agent are used in a weight ratio comprised between 1:1 and 5:1.

6. The process according to claim 1 wherein at least one polyisocyanate is selected from the group consisting of a polyisocyanurate of toluene diisocyanate, a trimethylol propane-adduct of toluene diisocyanate, a trimethylol propane-adduct of xylylene diisocyanate, a trimer of hexamethylene diisocyanate, a trimer of isophorone diisocyanate, a trimethylol propane-adduct of hexamethylene diisocyanate, a biuret of hexamethylene diisocyanate and mixtures thereof.

7. The process according to claim 1 wherein at least one polyisocyanate is used in an amount comprised between 2 and 30% by weight, relative to the total weight of the oil phase.

8. The process according to claim 1 wherein the anionic emulsifier is selected from the group consisting of acylglycinate salts, polyvinyl alcohol, cellulose polymers, sodium dodecyl sulfate, polyvinyl pyrrolidone, anionic polyelectrolytes, bovine serum albumin and gum arabic.

9. The process according to claim 1 wherein the polyamine is selected from the group consisting of 1,2-diaminopropane, 1,2-diaminoethane, diethylenetriamine, water soluble guanidine salts, guanidine, tris-(2-aminoethyl)amine, N,N'-bis(3-aminopropyl)-ethylenediamine, N,N,N',N'-tetrakis(3-aminopropyl)-1,4-butanediamine and 3,5-diamino-1,2,4-triazole.

10. The process according to claim 1 wherein the active ingredient is a perfume with a concentration comprised between 20 and 50% by weight relative to the total weight of the microcapsules slurry.

11. The process according to claim 1 wherein the microcapsules obtained comprise between 100 and 10000 ppm of silver particles.

12. Antimicrobial core-shell polyurea-based microcapsules obtainable by process as defined in claim 1, said microcapsules comprising:
 a polyurea-based wall, which comprises the reaction product of the polymerization between at least one polyisocyanate and at least one polyamine;
 a silver particle on or in the polyurea-based wall;
 an anionic emulsifier; and
 an encapsulated active ingredient;
 wherein the silver particles are generated during the interfacial polymerisation.

13. The antimicrobial polyurea-based microcapsules according to claim 12, characterized in that the size of silver particles is between 5 and 500 nm.

14. A perfuming composition comprising
 a) as perfuming ingredient, microcapsules according to claim 12;
 b) at least one ingredient selected from the group consisting of a perfumery carrier and a perfumery co-ingredient.

15. A perfuming consumer product comprising as a perfuming ingredient, a perfuming composition according to claim 14.

16. A perfuming consumer product according to claim 15, in the form of a deodorant or antiperspirant, a fabric or air refresher, a hard surface cleanser and deodorizer, a non-woven fabric and a cat litter.

17. A perfuming composition comprising
 c) as perfuming ingredient, microcapsules according to claim 13;
 d) at least one ingredient selected from the group consisting of a perfumery carrier and a perfumery co-ingredient.

18. A perfuming consumer product comprising as a perfuming ingredient a perfuming composition according to claim 17.

19. A process for the preparation of antimicrobial polyurea-based core-shell microcapsules comprising the following steps:
 a) dissolving at least one polyisocyanate in a perfume to form an oil phase;
 b) forming an oil-in-water emulsion by dispersing the oil phase into an aqueous solution comprising an anionic emulsifier;
 c) adding to the oil-in-water emulsion a polyamine, a silver salt and a reducing agent with the reducing agent added after the silver salt to form microcapsules with polyurea-based walls comprising silver particles in and on the walls.

20. Antimicrobial core-shell polyurea-based microcapsules obtainable by process as defined in claim 19, said microcapsules comprising:
 a polyurea-based wall, which comprises the reaction product of the polymerization between at least one polyisocyanate and at least one polyamine;
 a silver particle on and in the polyurea-based wall;
 an anionic emulsifier; and
 an encapsulated perfume;
 wherein the silver particles are generated during the interfacial polymerisation.

* * * * *

UNITED STATES PATENT AND TRADEMARK OFFICE
CERTIFICATE OF CORRECTION

PATENT NO. : 9,968,096 B2
APPLICATION NO. : 15/322040
DATED : May 15, 2018
INVENTOR(S) : Jerri et al.

It is certified that error appears in the above-identified patent and that said Letters Patent is hereby corrected as shown below:

On the Title Page

Item (56) References Cited, FOREIGN REFERENCES:
After "GB", delete "62432843" and insert -- 2432843 --; and
After "WO", delete "WO2008018684" and insert -- WO2008016684 --.

Signed and Sealed this
Twenty-sixth Day of June, 2018

Andrei Iancu
*Director of the United States Patent and Trademark Office*